United States Patent
Sherman et al.

[19]

[11] Patent Number: 6,010,500
[45] Date of Patent: Jan. 4, 2000

[54] TELESCOPING APPARATUS AND METHOD FOR LINEAR LESION ABLATION

[75] Inventors: Darren Sherman, San Jose; Mark L. Pomeranz, Los Gatos; Troy J. Chapman, Sunnyvale; N. Parker Willis, Atherton; Dale Rieb; Robert B. West, both of Sunnyvale, all of Calif.

[73] Assignee: Cardiac Pathways Corporation, Sunnyvale, Calif.

[21] Appl. No.: 08/897,567

[22] Filed: Jul. 21, 1997

[51] Int. Cl.$^7$ ..................................................... A61B 17/39
[52] U.S. Cl. ................................ 606/41; 606/49; 607/101
[58] Field of Search ........................... 606/41–42, 45–50; 607/98–101, 122

[56] References Cited

U.S. PATENT DOCUMENTS

| | | |
|---|---|---|
| 3,044,836 | 7/1962 | Conlon . |
| 4,850,351 | 7/1989 | Herman et al. . |
| 4,945,912 | 8/1990 | Langberg . |
| 4,979,948 | 12/1990 | Geddes et al. . |
| 5,191,883 | 3/1993 | Lennox et al. . |
| 5,230,349 | 7/1993 | Langberg . |
| 5,234,004 | 8/1993 | Hascoet et al. . |
| 5,236,413 | 8/1993 | Feiring . |
| 5,281,213 | 1/1994 | Milder et al. . |
| 5,334,193 | 8/1994 | Nardella . |
| 5,336,178 | 8/1994 | Kaplan et al. . |
| 5,342,357 | 8/1994 | Nardella . |
| 5,348,554 | 9/1994 | Imran et al. . |
| 5,368,597 | 11/1994 | Pagedas . |
| 5,383,876 | 1/1995 | Nardella . |
| 5,423,811 | 6/1995 | Imran et al. . |
| 5,443,470 | 8/1995 | Stern et al. . |
| 5,454,370 | 10/1995 | Avitall . |
| 5,487,385 | 1/1996 | Avitall . |
| 5,505,730 | 4/1996 | Edwards . |
| 5,569,241 | 10/1996 | Edwards . |
| 5,578,067 | 11/1996 | Ekwall et al. . |
| 5,584,872 | 12/1996 | Lafontaine et al. . |
| 5,697,927 | 12/1997 | Imran et al. ............................ 606/41 |

FOREIGN PATENT DOCUMENTS

| | | |
|---|---|---|
| 0 499 491 A2 | 8/1992 | European Pat. Off. . |
| 0 539 125 A1 | 4/1993 | European Pat. Off. . |
| 1466248 | 1/1967 | France . |
| 30 38 885 A1 | 5/1982 | Germany . |
| 1690786 A1 | 11/1991 | U.S.S.R. . |
| WO90/07909 | 7/1990 | WIPO . |
| WO 94/08519 | 4/1994 | WIPO . |
| WO95/34346 | 12/1995 | WIPO . |
| WO 96/00041 | 1/1996 | WIPO . |
| WO 96/00042 | 1/1996 | WIPO . |

OTHER PUBLICATIONS

Borggrefe, M. et al., "High Frequency Alternating Current Ablation of an Accessory Pathway in Humans," JACC vol. 10, No. 3, pp. 576–582 (Sep. 1987).

Abstracts 17A, JACC, vol. 11, No. 2, 3 pp. (Feb. 1988).

*Primary Examiner*—Michael Peffley
*Assistant Examiner*—Roy Gibson
*Attorney, Agent, or Firm*—Limbach & Limbach

[57] ABSTRACT

A catheter device for creating linear lesions in endocardial tissue or other body tissue is described. The catheter includes an inner shaft telescopically received within an outer shaft. The inner shaft has one or more spaced apart electrodes along its distal section. The outer shaft member includes a fluid permeable window positionable to selectively overlay some or all of the electrodes when the relative positioning of the inner and outer shaft members is adjusted. During use, the window is positioned adjacent to the body tissue which is to be ablated and at least a portion of the electrodes are exposed through the window. RF energy is delivered to the electrodes while saline or other conductive fluid is simultaneously delivered through the infusion tube. The conductive fluid passes into contact with the electrodes, and through the window into contact with the body tissue, thereby improving the coupling of the RF energy from the electrodes to the tissue and improving the efficiency of the ablation of the tissue.

33 Claims, 14 Drawing Sheets

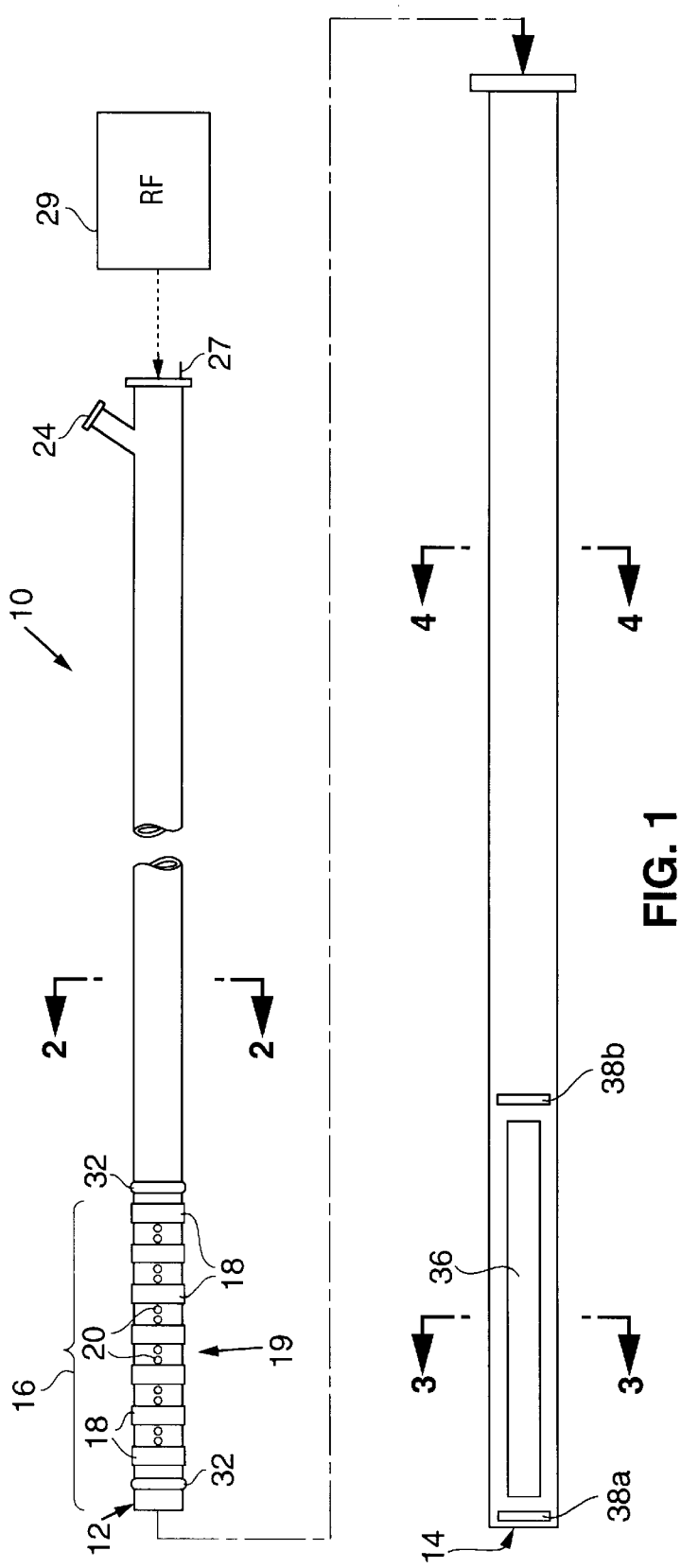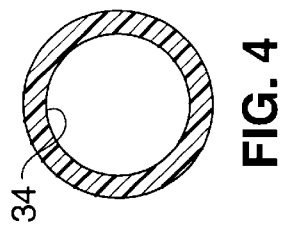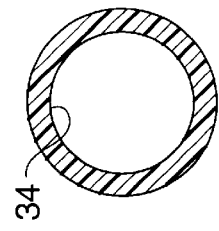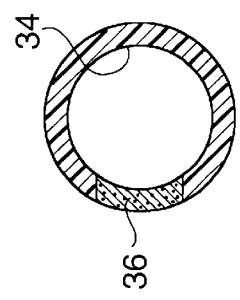
FIG. 1
FIG. 2
FIG. 3
FIG. 4

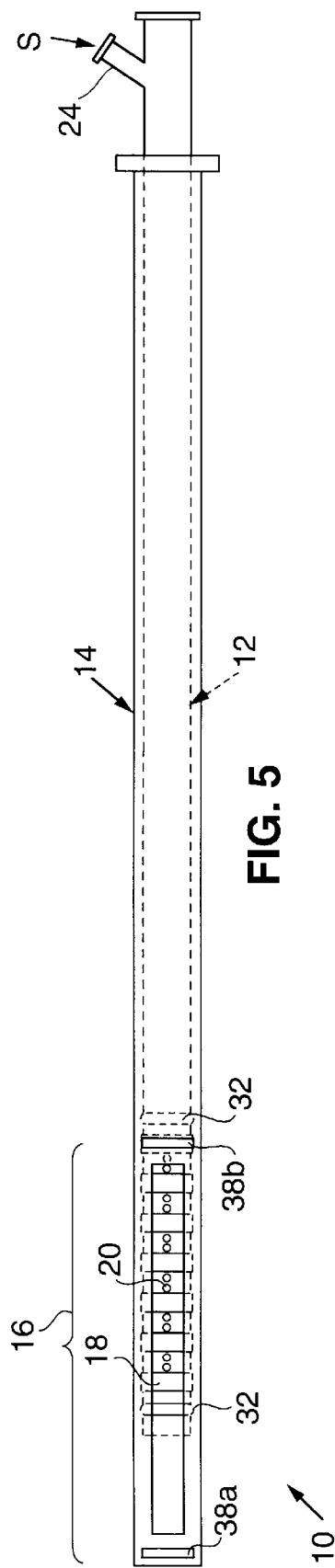
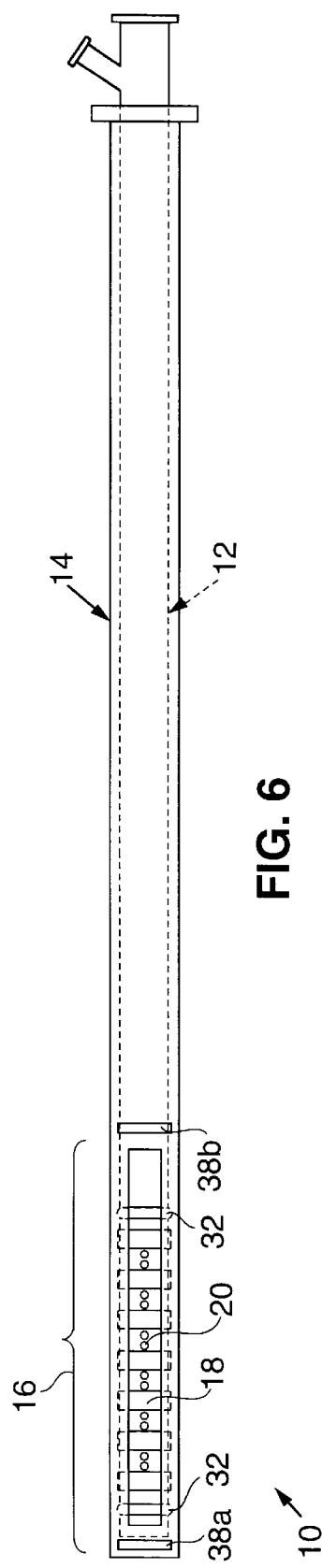
FIG. 5
FIG. 6

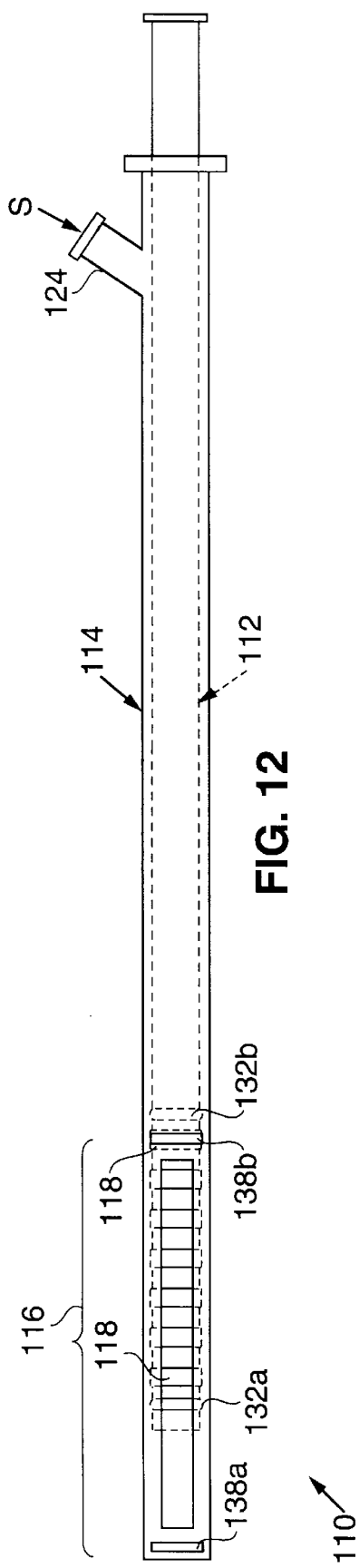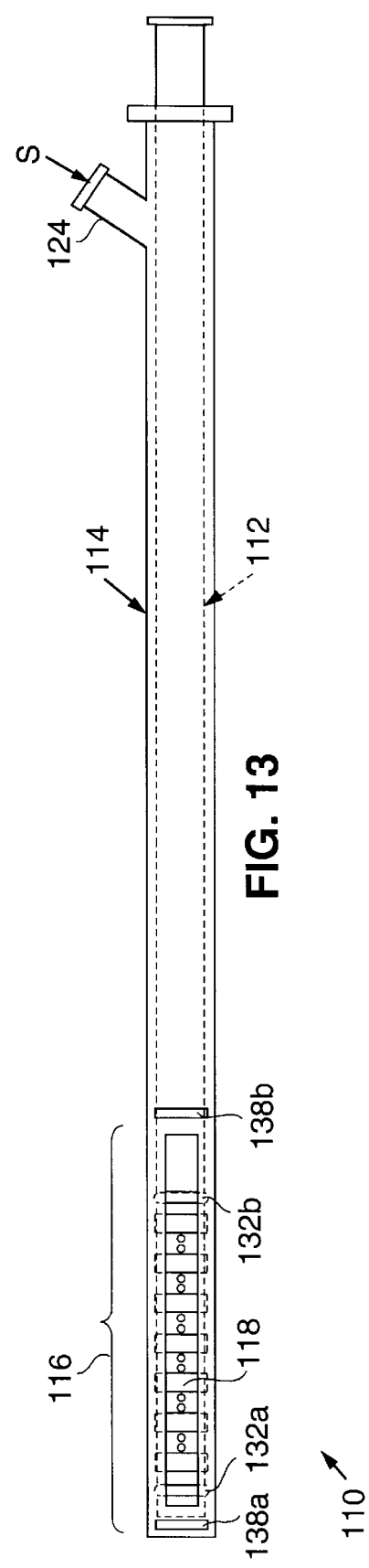

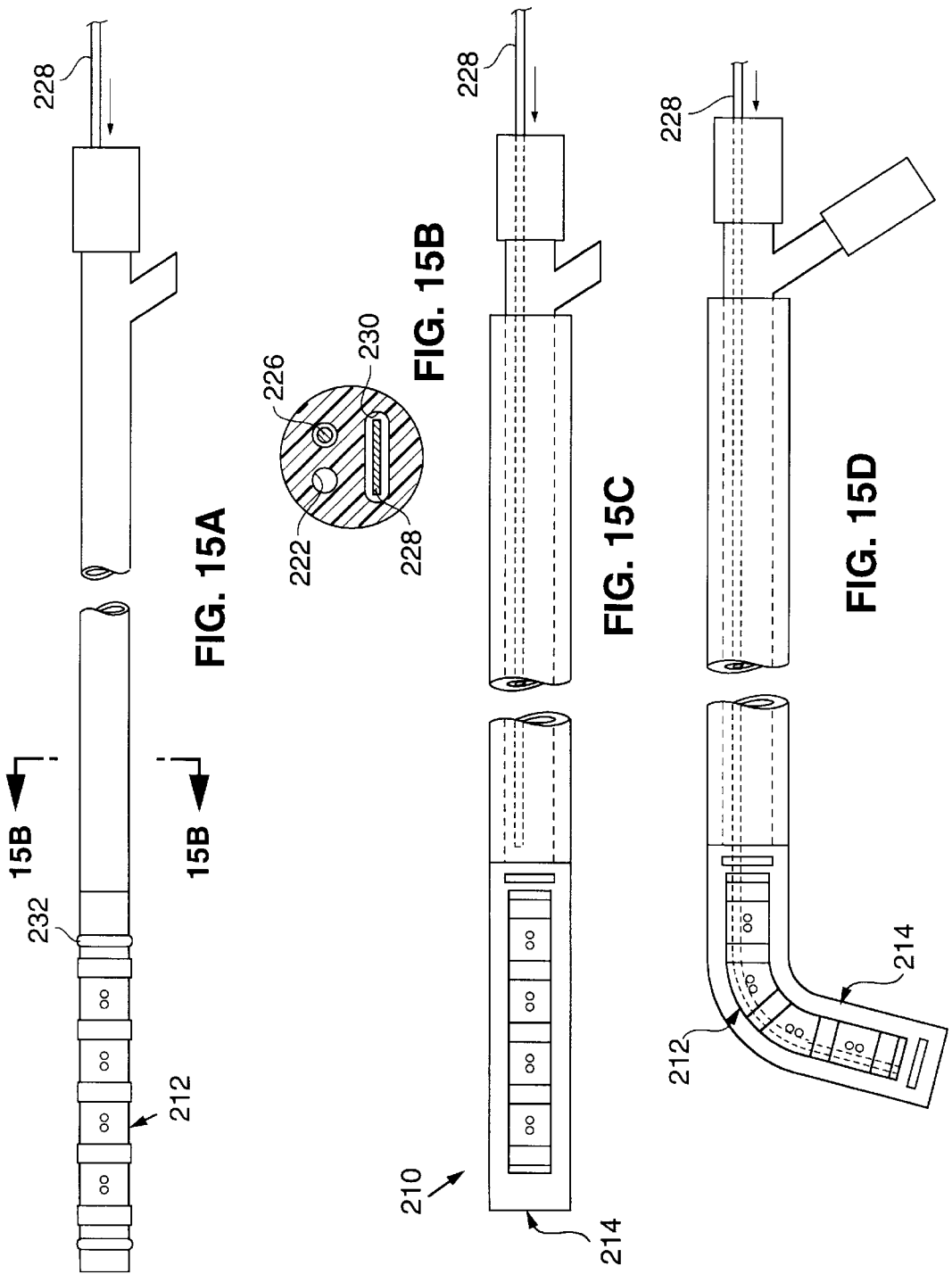

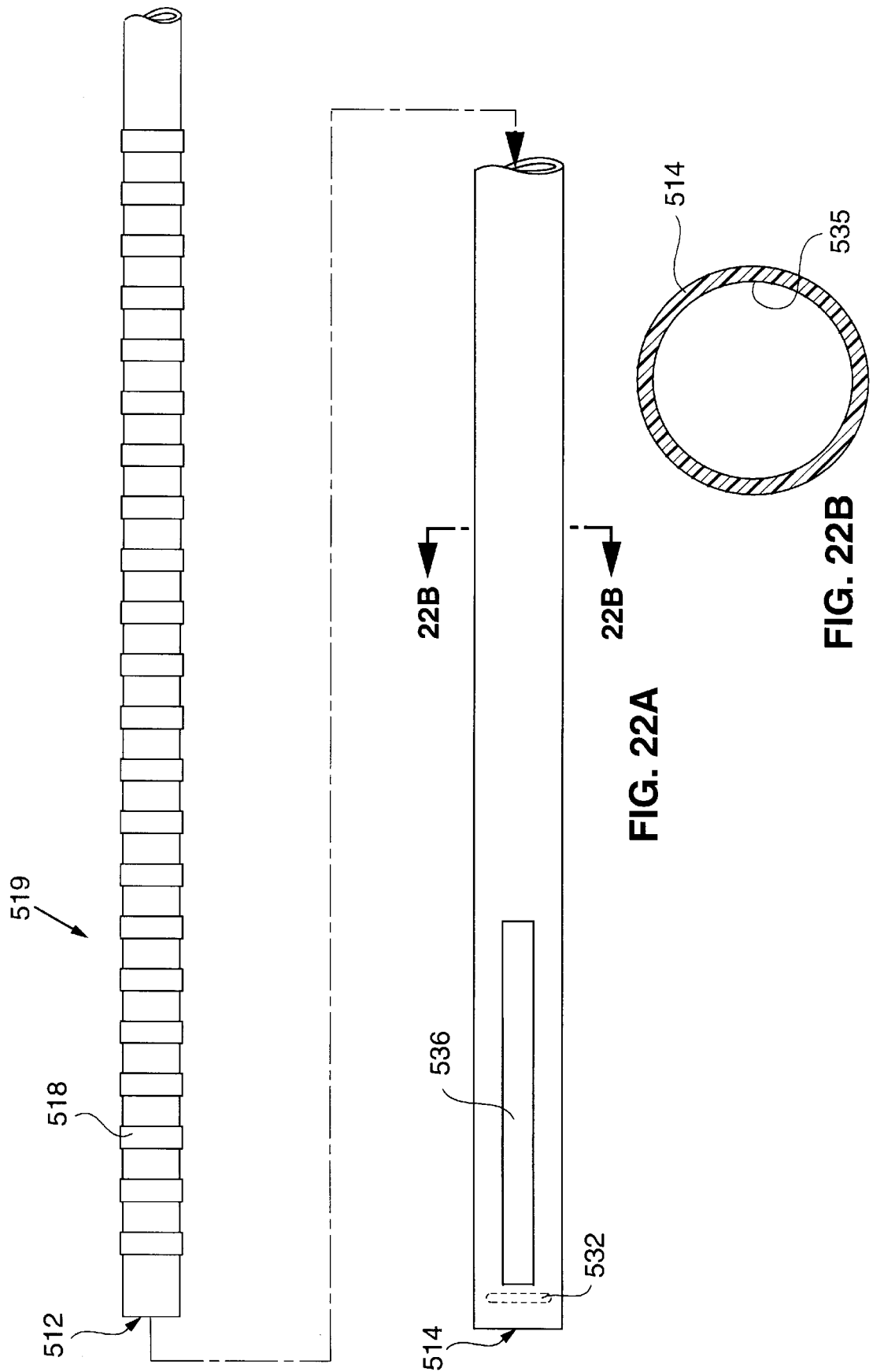

TELESCOPING APPARATUS AND METHOD FOR LINEAR LESION ABLATION

FIELD OF THE INVENTION

The present invention relates generally to the field of apparatuses and methods for ablating living tissue. In particular, the present invention relates to the field of devices and methods for creating linear lesions within the heart.

BACKGROUND OF THE INVENTION

Atrial fibrillation is a condition of the heart in which abnormal electrical signals are generated in the endocardial tissue to cause irregular beating of the heart. One method used to treat atrial fibrillation involves creating several long (i.e. approximately 2–10 cm) lesions on the endocardium within the atria. These lesions are intended to stop the irregular beating of the heart by creating barriers between regions of the atria. The barriers halt the passage through the heart of the abnormal currents generated by the endocardium. This procedure is commonly referred to as the "maze procedure" because it creates a maze of lesions designed to block the passage of abnormal currents through the heart.

Existing procedures for forming such linear lesions include the highly invasive technique of opening the patient's chest and heart and forming linear incisions inside the atria. Naturally, the highly invasive nature of this procedure makes it a particularly high risk to the patient and necessitates extraordinarily long recovery time.

Other attempts have been made to form the linear lesions using ablation catheters fed into the heart via the patient's vessels (i.e., the arteries or veins). For example, one such procedure involves inserting into the atria a 7 French catheter having an ablation tip. Radio frequency (RF) energy is supplied to the tip as the tip is dragged across the endocardium, thereby burning linear lesions into the endocardium.

While often successful for forming linear lesions, the ablation tip of the catheter can sometimes lift off of the surface of the endocardium as it is dragged across the endocardium, creating one or more breaks in the lesion. Such breaks minimize the success of the ablation procedure by leaving a path through which current may travel during atrial fibrillation episodes.

The ablation tip of the catheter can sometimes overheat, causing blood/tissue to coagulate around the metal tip. This can create a potential safety risk of an embolic event.

Procedures and devices for forming linear lesions within the atria are therefore desired which will block the passage of current through the heart during atrial fibrillation episodes, as with the surgical incision procedure, but which utilize the less-invasive technique of a percutaneous catheter. Further desirable is a linear lesion catheter having the flexibility and maneuverability of the electrode tipped catheter but which generates a continuous lesion on the endocardium.

It is further desirable to improve the continuity and thus the effectiveness of linear lesions formed using ablation catheters by providing means by which a linear lesion catheter may be held securely against endocardial tissue during ablation, by which electrical energy may be focussed from the ablation electrodes onto the endocardium, and by which the desired length of the linear lesion may be selected by the user.

SUMMARY OF THE INVENTION

The present invention is a catheter device for creating linear lesions in endocardial tissue or other body tissue. The catheter includes an inner shaft member having an ablation section at which one or more spaced apart electrodes are carried.

Inner shaft member is telescopically received within an outer shaft member. The inner or outer shaft member includes a fluid lumen which delivers conductive liquid into contact with the electrodes. The outer shaft member includes a fluid permeable window.

During use, a distal portion of the apparatus is positioned adjacent to the body tissue which is to be ablated. The relative positioning of the inner and outer shaft members is adjusted such that the window is positioned adjacent to the tissue to be treated and such that the window is over at least a portion of the electrodes on the inner shaft.

RF energy is delivered to the electrodes while saline or other conductive fluid is simultaneously delivered through the infusion tube. The conductive fluid from the fluid lumen into contact with the electrodes. The fluid also flows through the window into contact with the body tissue, thereby improving the coupling of the RF energy from the electrodes to the tissue and improving the efficiency of the ablation of the tissue.

Utilizing a conductive liquid which is dispersed over the desired area as a mechanism for coupling RF energy to the tissue produces lesions having greater continuity (and thus fewer breaks through which current can pass during atrial fibrillation episodes) than lesions formed by prior art apparatuses which rely solely on direct contact between the electrodes and the body tissue. The conductive liquid also cools the electrodes, decreasing the likelihood of thrombus formation on the electrodes and thus decreasing the chance of embolism. The arrangement of the inner and outer shaft members and the window helps to direct the conductive liquid onto a desired region of the endocardium and therefore helps to focus the RF energy onto that same desired region.

BRIEF DESCRIPTION OF THE DRAWINGS

FIG. 1 is a side elevation view of a first embodiment of a linear lesion catheter according to the present invention, in which the inner and outer shafts are separated from one another.

FIG. 2 is a cross-section view of the inner shaft member of the linear lesion catheter of FIG. 1, taken along the plane designated 2—2 in FIG. 1.

FIG. 3 is a cross-section view of the distal portion of the outer shaft of the linear lesion catheter of FIG. 1, taken along the plane designated 3—3 in FIG. 1.

FIG. 4 is a cross-section view of the proximal section of the outer shaft of the linear lesion catheter of FIG. 1, taken along the plane designated 4—4 in FIG. 1.

FIG. 5 is side elevation view of the ablation section of the linear lesion catheter of FIG. 1, showing the inner and outer shafts positioned to expose a portion of the electrodes through the window.

FIG. 6 is side elevation view of the ablation section of the linear lesion catheter of FIG. 1, showing the inner and outer shafts to expose all of the electrodes through the window.

FIG. 12 is side elevation view of the linear lesion catheter of FIG. 7, showing the inner and outer shafts positioned to expose a portion of the electrodes through the window.

FIG. 13 is side elevation view of the ablation section of the linear lesion catheter of FIG. 7, showing the inner shaft positioned within the outer shaft in a manner which exposes all of the electrodes through the window.

FIG. 15A is a side elevation view of the inner shaft of the embodiment of FIG. 14, showing insertion of the shaped core into the inner shaft.

FIG. 15B is a cross section view of the inner shaft taken along the plane designated 15B–15B in FIG. 15A.

FIG. 15C is a side elevation view of the linear lesion catheter of FIG. 14, showing insertion of the inner shaft into the outer shaft and further showing insertion of the shaped core into the inner shaft.

FIG. 15D is a side elevation view of the linear lesion catheter of FIG. 14 showing the orientation of the inner and outer shafts following insertion of the shaped core into the inner shaft.

FIG. 22A is a side elevation view of a sixth embodiment of a linear lesion catheter according to the present invention, in which the inner and outer shaft members are separated from one another.

FIG. 22B is a cross-section view of the outer shaft taken along the plane designated 22B–22B in FIG. 22A.

DETAILED DESCRIPTION OF EXEMPLARY EMBODIMENTS

Figure 7:
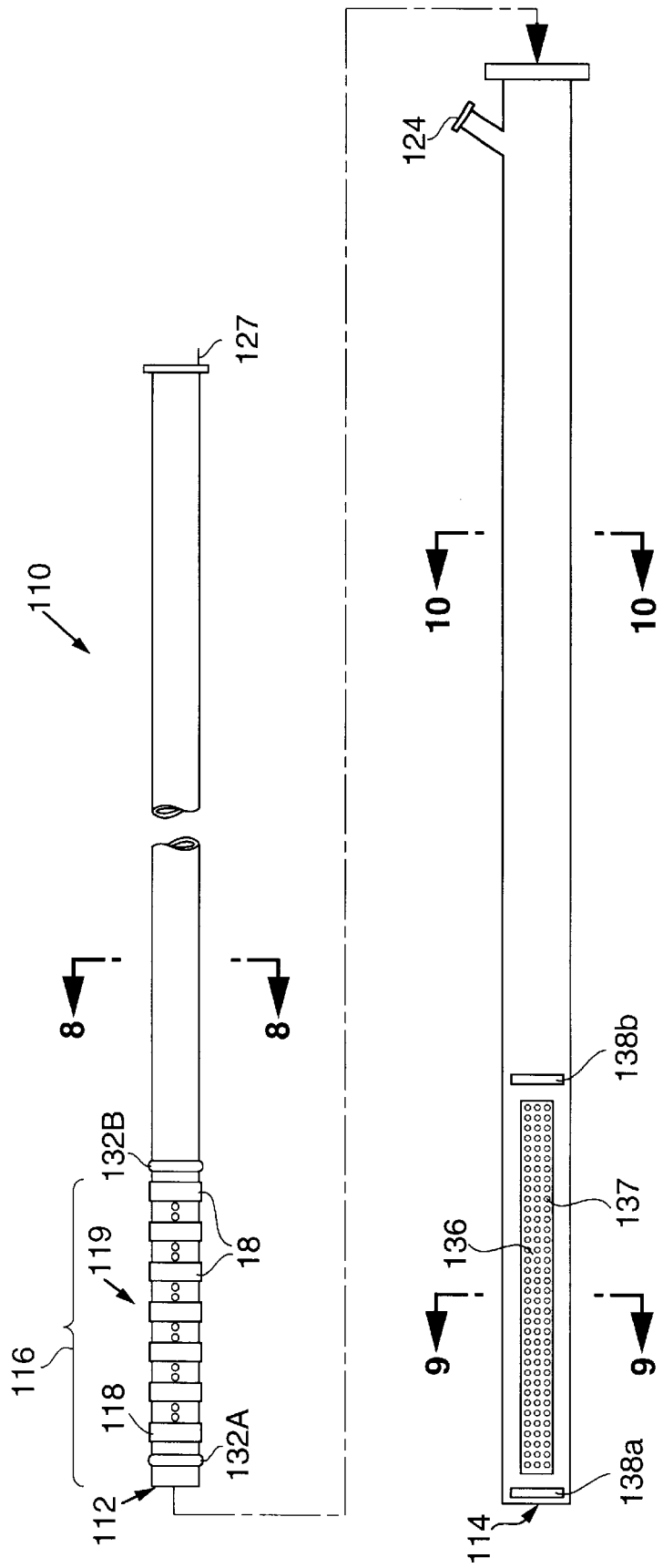
FIG. 7 is a side elevation view of a second embodiment of a linear lesion catheter according to the present invention, in which the inner and outer shafts are separated from one another.
Figure 8:
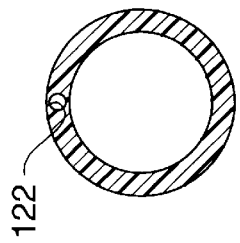
FIG. 8 is a cross-section view of the inner shaft of the linear lesion catheter of FIG. 7, taken along the plane designated 8—8 in FIG. 7.
Figure 9:
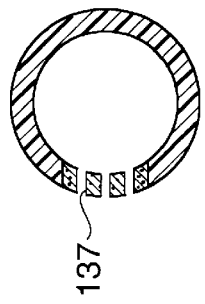
FIG. 9 is a cross-section view of the distal portion of the outer shaft of the linear lesion catheter of FIG. 7, taken along the plane designated 9—9 in FIG. 7.
Figure 10:
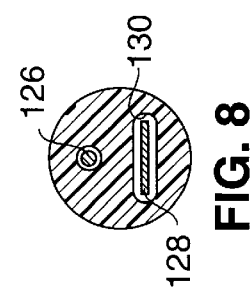
FIG. 10 is a cross-section view of the proximal section of the outer shaft of the linear lesion catheter of FIG. 7, taken along the plane designated 10—10 in FIG. 7.
Figure 11:
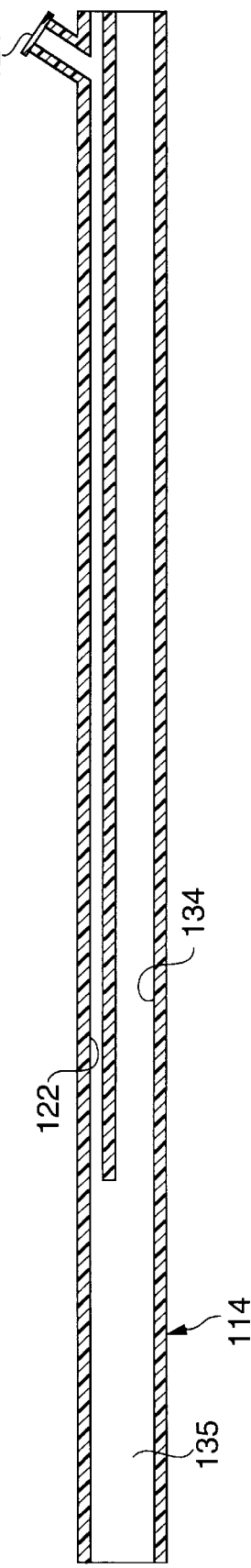
FIG. 11 is a cross-sectional side elevation view of the outer shaft of the linear lesion catheter of FIG. 7.

A first embodiment of a linear lesion catheter 10 according to the present invention is shown in FIG. 1. The catheter 10 is comprised generally of an inner shaft 12 and an outer shaft 14. Inner shaft 12 extends telescopically through the outer shaft 14.

The catheter 10 has an ablation section 16 located at the distal end. During use, the ablation section 16 is positioned against the target tissue to be ablated and delivers RF energy to the tissue to cause ablation. It should be appreciated that other types of ablation elements may be substituted for the RF ablation elements described in this and the following embodiments. For example, ultrasound ablation elements or other conventional ablation tips may be used in combination with some or all of the other features of the invention described herein without departing from the scope of the present invention.

Referring to FIG. 1, inner shaft 12 is an elongate shaft preferably formed of a thermoplastic polymer, polyamid ether, polyurethane, polyolefin, or other material having similar properties.

One or more spaced ring electrodes 18 each encircle the distal end of the inner shaft, forming an electrode array 19. Other types of electrodes may alternatively be used in electrode array of this and the other embodiments described herein. For example, spaced conductive strips or bands may be formed on the surface of the inner shaft, or wire coils, braids or other conductive material may be helically wound around the inner shaft.

The electrodes may also be formed from conductive wires or ribbons, each of which is covered by an insulated coating having exposed electrode regions that are stripped of insulative material. Such flattened wires or ribbons may be advantageous in that they produce RF energy electric field lines which are not concentrated at the edges of the ribbons, but are instead dispersed along the entire length of the ribbon. Electrode wires or ribbons of this type may extend along the exterior of the shaft 12 or through the fluid lumen 22 (described below) in order to optimize RF fluid coupling between the electrodes and the target tissue.

A plurality of openings 20 are spaced along the distal end of the inner shaft 12 and are interspersed with the electrodes 18. The openings 20 may be formed on one side of the inner shaft as shown or they may be arranged in other patterns, such as circumferentially around the inner shaft 12.

Referring to FIG. 2, a fluid lumen 22 extends through the inner shaft 12. Fluid lumen 22 is fluidly coupled to the openings 20 and to a fluid port 24 located at the proximal end of the inner shaft 12. A lead wire 26 also extends through the inner shaft 12 and is electrically coupled to electrodes 18. RF energy is supplied to the lead wire 26 via a connector 27 which connects the inner shaft 12 to a conventional RF energy source 29 such as the Model 8002 RF Generator which is available from Cardiac Pathways Corporation, Sunnyvale, Calif. The electrodes may be used for uni-polar ablation using a grounding pad attached to the patient. Alternatively, the device may be configured for bi-polar ablation by providing a pair of leads and by attaching alternate electrodes to alternate ones of the leads.

A core wire 28 extends through a core lumen 30 of the inner shaft 12. Wire 28 may alternatively be a pull wire of a type which may be used to steer the catheter through a patient's vessels and heart. Wire 28 may also be a looped baffle wire or ribbon of the type described and shown in International Application PCT/US96/17536, the disclosure of which is incorporated herein by reference. The inner shaft 12 would then be slidable over the baffle wire to position the catheter within the heart chamber. Wire 28 and lumen 30 are preferably oblong in cross-section to prevent rotation of the wire within the lumen.

O-ring gaskets 32 surrounds the inner shaft 12 near the distal end of the shaft on opposite ends of the electrode array.

Referring again to FIG. 1, outer shaft 14 is an elongate tube having a central lumen 34 (FIGS. 3 and 4) for telescopically receiving the inner shaft 12. The outer shaft may have an open distal end as shown in FIGS. 1–6 or it may have a closed distal end as shown with respect with the third embodiment in FIGS. 14–17. It should be noted that if the distal end is closed, only the more proximal of the o-ring seals 32 is needed.

The outer shaft 14 is preferably formed of a thermoplastic polymer, polyamid ether, polyurethane or other material having similar properties. It may be configured in a variety of ways, depending on the location within the heart at which the procedure is to be conducted. For example, the outer shaft 14 may be flexible to facilitate movement of the catheter 10 through a patient's vasculature and into the cardiac chamber. It may have a distal section which is pre-shaped to facilitate contact between the shaft and the target cardiac tissue during ablation. It may also include a stainless steel braid embedded in its walls by means conventionally known in the art in order to improve the torque characteristics of the shaft and to thus make it easier to maneuver through a patient's vessels and heart.

A window 36 (FIGS. 1 and 3) is formed in the outer shaft 14 near the distal end. The window 36 is formed in a manner which permits fluid to flow out of the outer shaft via the window. For each of the described embodiments, the window is preferably a cutout section covered with a porous material (FIG. 3) such as porous mesh or heat shrink polyethylene, silicone, or other polymeric materials having a plurality of small holes or perforations. It may also be an area of the outer shaft which is provided with a plurality of tiny holes as shown with respect to the second embodiment in FIG. 7. The plurality of tiny holes or the porous material allows for more even distribution of the fluid flow and reduces the chance that blood can enter the shaft member through the window. Alternatively, the window may be simply a cutout section of the outer shaft without any additional covering. Additional windows may be provided to be spaced circumferentially and/or longitudinally of the window 36.

Radiopaque markers 38a, 38b are positioned adjacent to the window 36 so that the location of the window can be detected under fluoroscopy. Preferably, the markers 38a, 38b are also mapping/pacing electrodes.

During use of the catheter 10 of FIGS. 1 through 6, the inner shaft 12 is first inserted telescopically into the lumen 34 of the outer shaft 14. The O-ring seals 32 on the inner shaft contact the interior surface of outer shaft lumen 34. This creates fluid tight seals between the inner and outer shafts at the ablation section 16 of the catheter 10.

Next, catheter 10 is inserted through a patient's vasculature to position ablation section 16 within the cardiac chamber in which ablation is to be performed. The ablation section 16 is positioned, preferably under fluoroscopy(with the markers 38 being used to identify the proximal and distal ends of the window section 36), against the tissue so that the window section 36 of the outer shaft 14 is adjacent to the target cardiac tissue. The relative positions of the inner and outer shafts 12, 14 are adjusted by sliding one relative to the other, to position some (FIG. 5) or all (FIG. 6) of the electrodes 18 and openings 20 within the window section 36.

The ablation section 16 is next positioned such that the window 36 is adjacent to the target tissue. Delivery of RF energy to the endocardial tissue is commenced once window 36 is in contact with the desired region of the endocardial surface. It may be desirable to configure the radiopaque markers 38a, 38b to also serve as electrical pacing/mapping catheters so that contact between the catheter 10 and the cardiac tissue over the length of the ablation section 16 may be assessed prior to and during ablation.

Contact between the outer sheath and the underlying tissue may be evaluated by applying a unipole electrical stimulus (a pacing pulse) between electrode/marker 38a and another electrode (not shown), such as a reference patch attached to the patient or an electrode on a separate catheter located in the patient's vasculature, in the heart in order to stimulate the tissue. Similarly the contact can be assessed at the other end of the ablation section 16 by applying an electrical stimulus (a pacing pulse) between electrode/marker 38b and another electrode, not shown, in the heart in order to stimulate the tissue. This contact evaluation is made by 1) applying sufficient current between the electrodes to effect the stimulation of the tissue and recording that level of current and 2) assessing the current levels required for stimulation. A relatively low level of current such as 0.5 to 2 milliamps is required to stimulate the tissue if the electrode 38a or 38b is in contact with the tissue.

RF energy from an RF generator is delivered to electrodes 18 via lead 26. At the same time, conductive fluid, such as saline S (FIG. 5), is directed into port 24 and through infusion lumen 22. It may also be desirable to begin to apply positive fluid pressure even before RF ablation is commenced, in order to prevent blood accumulation in or on the window surface 36 if the window is formed of a porous material rather than a cutout.

The saline passes through holes 20 in the inner shaft and into lumen 34 of the outer shaft 14. The O-ring seals 32 prevent the saline from passing between the shafts 12, 14 in a proximal or distal direction and cause the saline to pool between the seals 32 and to exit the catheter 10 via the window 36. As the saline moves from the holes 20 to the window, it creates a conductive path (for passage of the RF energy) between the electrodes 18 and the endocardium. The RF energy travels along this conductive path from the electrodes into the tissue. Once a lesion has been formed at the target spot, the catheter 10 may be repositioned within the selected chamber of the heart and additional lesions formed.

The window 36 therefore serves as the conduit through which electrolytic solution passes from the catheter to the endocardium. The fluid flow through the openings or pores in the window focuses the RF energy onto the tissue. The dimensions and arrangement of the openings/pores in the window are selected to insure infusion of saline and delivery of RF energy to the underlying tissue. The distribution of the openings in the window should be limited to that which will create a continuous transmural linear lesion over the desired ablation surface. It has been found desirable to use hole/pore sizes of approximately between 0.003 to 0.020 inches.

The positioning of the window 36 so that it extends only along one side of the outer shaft 14 (i.e., the side which, during use, will be positioned against the target ablation site) helps to focus the RF energy in that is prevents the RF energy from being lost into the blood pool.

Although it is preferred to utilize the conductive fluid or saline in a manner in which the conductive fluid creates a conductive path between the electrodes and the target tissue, saline may alternatively or additionally be utilized in the present invention to cool the ablation electrodes. Moreover, the present invention may also be used without an electrolytic solution, in which case direct contact between the electrodes 18 and the target cardiac tissue would be made through the window 36.

Once a lesion is formed, it may be evaluated by applying an electrical signal to electrode/marker 38a. To evaluate whether an effective lesion has been formed in the tissue, a comparison of the electrical response of the tissue taken before the ablation to the electrical response of the tissue taken after the lesion is formed can be made. This comparison is made by 1) recording a unipole signal amplitude/potential between electrode/marker 38a and another electrode (not shown), such as a reference patch attached to the patient or an electrode on a separate catheter located in the patient's vasculature, 2) recording a unipole signal amplitude/potential between electrode/marker 38b and another electrode, not shown, 3) applying RF energy through window 36, 4) recording the two unipole signal amplitudes/potentials again, and 5) comparing the signal amplitude and signal morphology of the recordings before the ablation to the recordings after the ablation. A reduction in signal amplitude indicates that the tissue in the area of the electrode/marker has been modified by the ablation.

The evaluation can also be made by applying a unipole electrical stimulus (a pacing pulse) between electrode/marker 38a and another electrode, not shown and by applying an electrical stimulus (a pacing pulse) between electrode/marker 38b and another electrode, not shown. This comparison is made by 1) applying sufficient current between the electrodes to effect the stimulation of the tissue and recording that level of current; 2) applying RF energy through the window 36; 3) applying sufficient current between the electrodes to effect the stimulation of the tissue and recording that level of current or recording that the stimulation could not be accomplished with reasonable current levels; and 4) comparing the current levels required for stimulation before and after the ablation. An increase in the required current levels indicates that the tissue in the area of the electrode/marker has been modified by the ablation.

A second linear lesion catheter 110 according to the present invention is shown in FIGS. 7 through 13.

Referring to FIG. 7, catheter 110 is comprised of inner and outer shafts 112, 114. The inner shaft 112 has a plurality of spaced electrodes 118 at its distal end and it differs from the inner shaft 12 of the first embodiment in that it is provided without an infusion lumen (see lumen 22 of FIG. 2) or holes (see holes 20 of FIG. 1). As with the first embodiment, the inner shaft 112 includes an electrode lead 126, a core wire 128, a core wire lumen 130, and an O-ring seals 132a, 132b.

Outer shaft 114 of the second embodiment differs from that of the first embodiment in that it is configured to deliver electrolytic solution to the ablation section 116 for contact with the electrodes 118. Referring to FIG. 7, outer shaft 114 includes a window 136 which directs the flow of electrolytic solution onto adjacent cardiac tissue. In this embodiment, the window is comprised of a plurality of tiny holes 137 formed in the outer shaft 114, although other porous materials may be used as described above. For clarity, the holes 137 are not shown in FIGS. 12 and 13.

A main lumen 134 extends the length of the outer shaft 114, and an infusion lumen 122 extends from the proximal end of the outer shaft 114 and opens into the main lumen 134 at a location adjacent to the window 136. The lumen 122, 134 combine to form a broader single lumen 135 at the ablation section 116.

Use of the second embodiment according to the present invention is similar to use of the first embodiment, except in the manner in which electrolytic solution is delivered into contact with the electrodes 118. During use of the second embodiment, the solution is introduced into the catheter via a fluid port 124 on the outer shaft 114 which is fluidly coupled with infusion lumen 122. When the solution passes from the fluid lumen 122 through the broadened section 135 of the outer shaft 114 (which is at the ablation section 116 of the catheter 110), it creates a conductive path between the electrodes 118 and the target cardiac tissue. Fluid is prevented from flowing proximally or distally of the window 136 by seal 132a which contacts the inner surface of single lumen 135 and by seal 132b which contacts the inner surface of main lumen 134.

The outer shaft 114 of the second embodiment may alternatively be provided without separate fluid lumen 122, in which case the outer shaft 114 would be a single lumen device with the single lumen serving as the fluid lumen. If a configuration of this type is used, the seal 132b would be eliminated so that fluid introduced into the distal end of the outer shaft 114 could flow into contact with the electrodes 118. See the embodiment of FIG. 22A.

FIGS. 14 through 17 illustrate a third embodiment of a linear lesion catheter 220 according to the present invention. This embodiment is similar to the first embodiment except that it is provided to be used in connection with an exchangeable core wire 228 in place of the core wire 28. Exchangeable core wire 228 allows the catheter 220 to be formed into a desired shape during its use. By allowing the ablation section of the catheter to be selectively shaped, contact between the ablation section and the target cardiac tissue may be enhanced during the ablation procedure.

Figure 14:
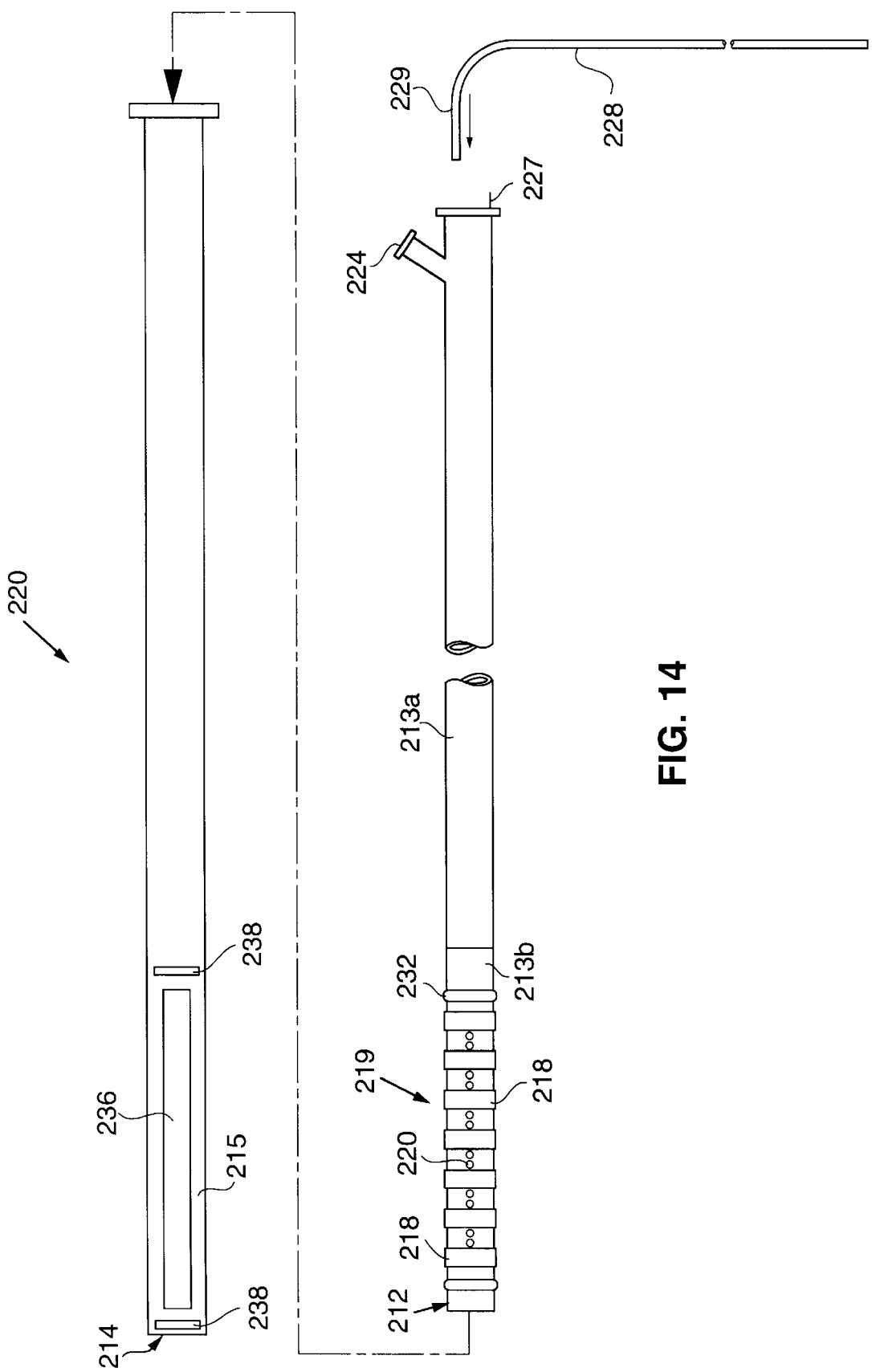
FIG. 14 is a side elevation view of a third embodiment of a linear lesion catheter, showing the outer shaft, inner shaft, and shaped core separated from one another.
Figure 16A:
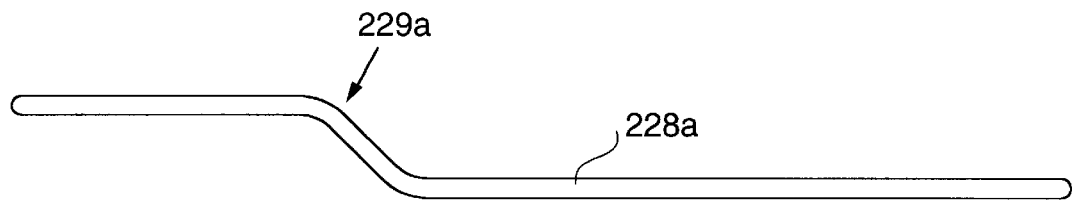
FIGS. 16A and 16B are side elevation views of alternative core wires for use with the embodiment of FIG. 14.
Figure 16B:
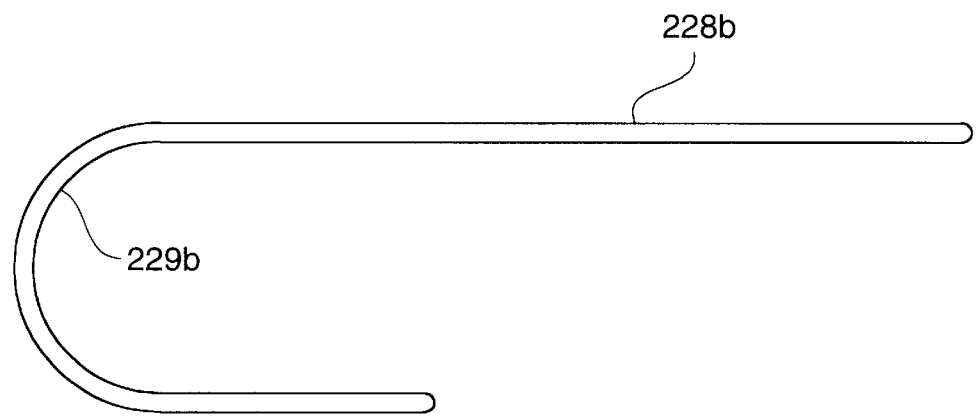
Figure 17A:
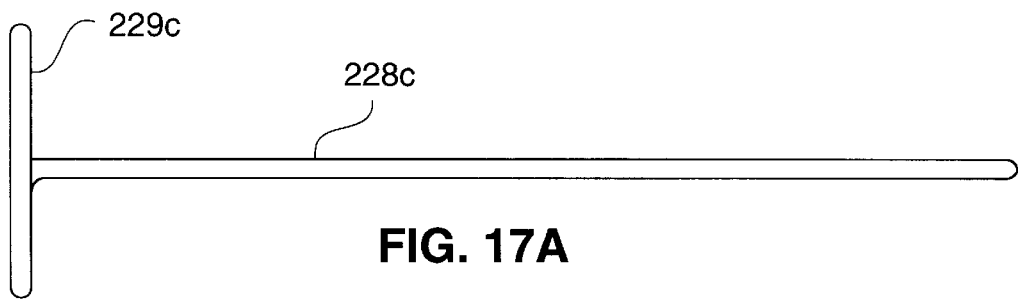
FIGS. 17A and 17B are a side elevation view and an end view, respectively, of an alternative core wire for use with the embodiment of FIG. 14.
Figure 17B:
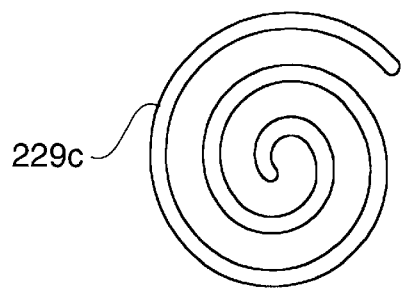

Referring to FIG. 14, core wire 228 is an elongate wire formed of a superelastic material such as Nitinol. Core wire 228 includes a pre-shaped section 229, preferably at its distal end. The pre-shaped section 229 may have the C-curve shown in FIG. 14, or it may have one of numerous other shapes including a Z- or S-curve (designated 229a in FIG. 16A), a J-curve (designated 229b in FIG. 16B), or a spiral shape (designated 229c in FIGS. 17A and 17B). The core wire 228 may alternatively be a shapable wire made of stainless steel that a surgeon may bend into a desired configured before inserting it into the inner shaft 212.

Although the core wire lumen 230 and core wire 228 may be formed to have a number of cross-sectional shapes, they preferably have oblong cross-sections to prevent rotation of the core wire within the lumen during use. See FIG. 15B.

The inner shaft 212 includes a proximal section 213a which is sufficiently rigid to straighten the core wire 228 when the core wire is disposed within the proximal section and a distal section 213b (at the ablation section 216) which has significantly greater flexibility than the proximal section. The material for the distal section 213b is selected to have a sufficiently low durometer or hardness (e.g., approximately 25–50 Shore D) to permit the distal section 213b to be highly flexible. In contrast, the proximal section 213a is formed of a higher durometer material (e.g., approximately 55–80 Shore D) and thus is fairly rigid.

Distal section 215 of the outer shaft 214 is formed of a flexible material similar to that of the distal section 213b of the inner shaft 212. The proximal section of the outer shaft 214 may be flexible or rigid.

Referring to FIGS. 15A–15C, during use, the core wire 228 is inserted into the proximal section 213a of lumen 30 (FIG.2) of the inner shaft 212. As the pre-shaped section 229 of the core wire 228 passes through the proximal section 213a of the catheter, the rigidity of the proximal section causes the pre-shaped region of the core wire to straighten.

Next, inner shaft 212 is inserted into the outer shaft 214 as shown in FIG. 15C and the catheter 210 is inserted into the desired cardiac chamber. The core wire 228 is then advanced further into the inner shaft 212. When the preshaped region 229 of the core wire 228 enters the flexible distal section 213b of the catheter, the characteristics of the superelastic core wire material cause the unrestricted core wire to return to its pre-formed shape and to cause the distal section of the catheter 210 to take the shape of the core wire. See FIG. 15D.

The relative positioning of the inner and outer shafts 212, 214 is adjusted as described with respect to the first embodiment, and the ablation procedure is carried out as described above.

Figure 18:
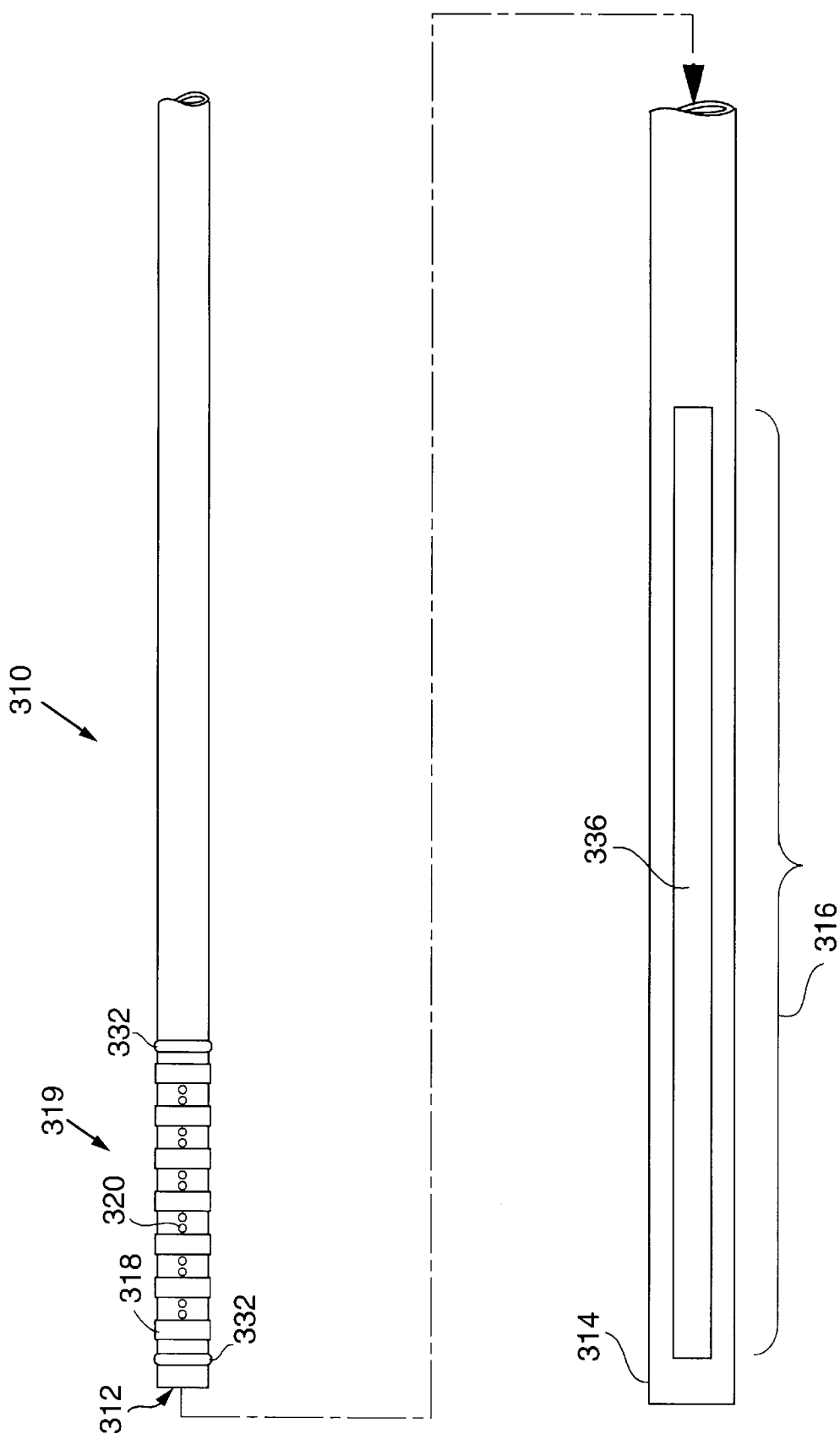
FIG. 18 is a side elevation view of a fourth embodiment of a linear lesion catheter according to the present invention, in which the inner and outer shaft members are separated from one another.
Figure 19A:
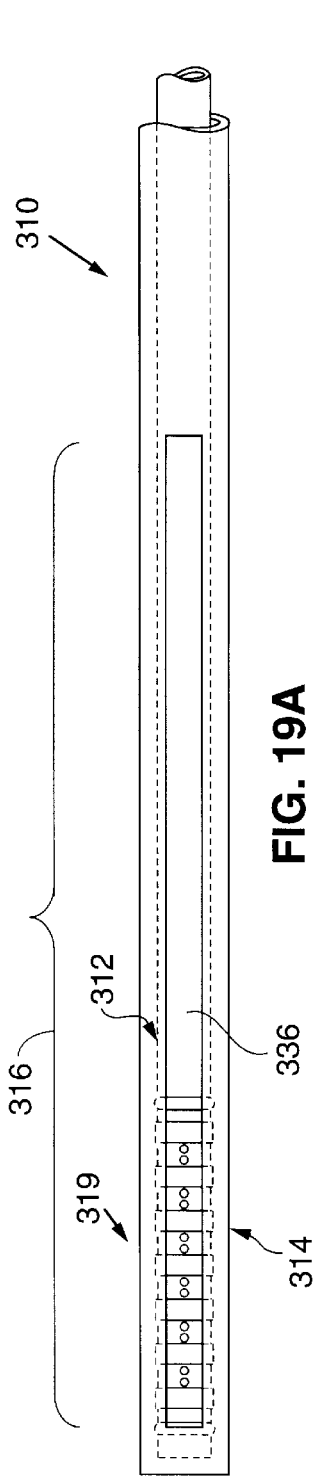
FIGS. 19A through 19C are side elevation views of the distal portion of the linear lesion catheter of FIG. 18, in which three relative positions of the inner and outer shaft members are shown.
Figure 19B:
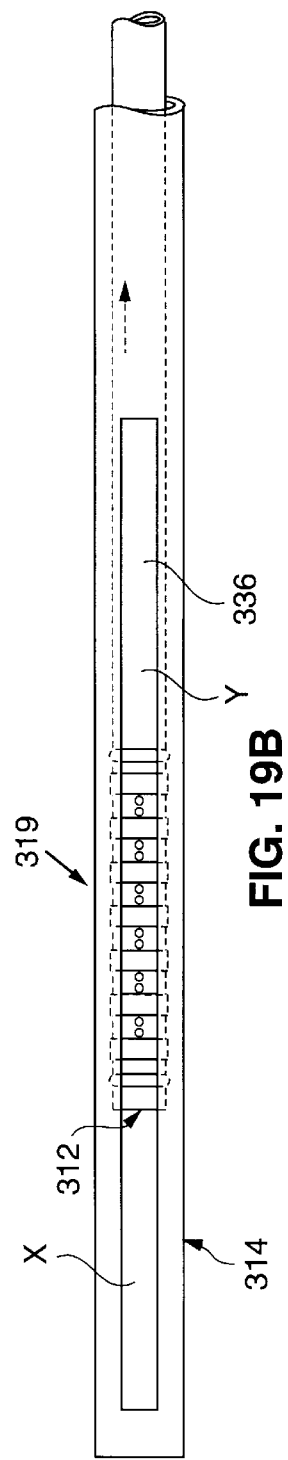
Figure 19C:
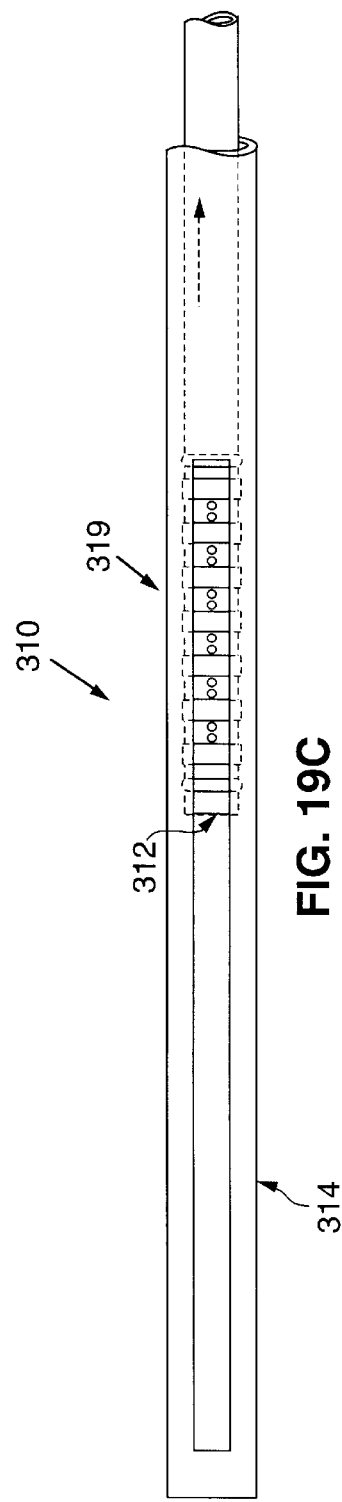

FIGS. 18 through 19C show a fourth embodiment of a telescoping linear lesion ablation catheter 310 according to the present invention. This embodiment differs from the first embodiment primarily in that window 336 in outer shaft 314 is longer, and preferably significantly longer, than the length of the inner shaft 312 upon which the electrodes 318 are located. The relatively long window 336 can be advantageous for a number of reasons. For example, if it is desired to create a long lesion, the physician can first create a lesion at one end of the window 336, as shown in FIG. 19A. Next, without moving outer shaft 314, the physician can slide the inner shaft relative to the outer shaft to position the electrode section of the inner shaft at a central region of the window as shown in FIG. 19B, and form a lesion at the central region. Finally, the inner shaft is again moved relative to the outer shaft to position the electrode section at the proximal end of the window 336 (FIG. 19C) and another lesion is formed. This procedure allows for the creation of a long lesion without requiring repositioning of the outer shaft.

Another advantage of the embodiment of FIG. 18 is that, even if a relatively short lesion is desired, the long window allows the physician to decide where along the length of the window to position the electrodes 318. This gives him or her greater flexibility to choose an ablation site without requiring repositioning of the outer shaft. Because the seals 332 are formed on the inner shaft, they prevent the conductive fluid from flowing to regions of the window which lay proximally and distally of the electrode array 319 (for example, the regions designated X and Y in FIG. 19B) and thus minimize the chance for ablation occurring outside of the desired area.

Figure 20:
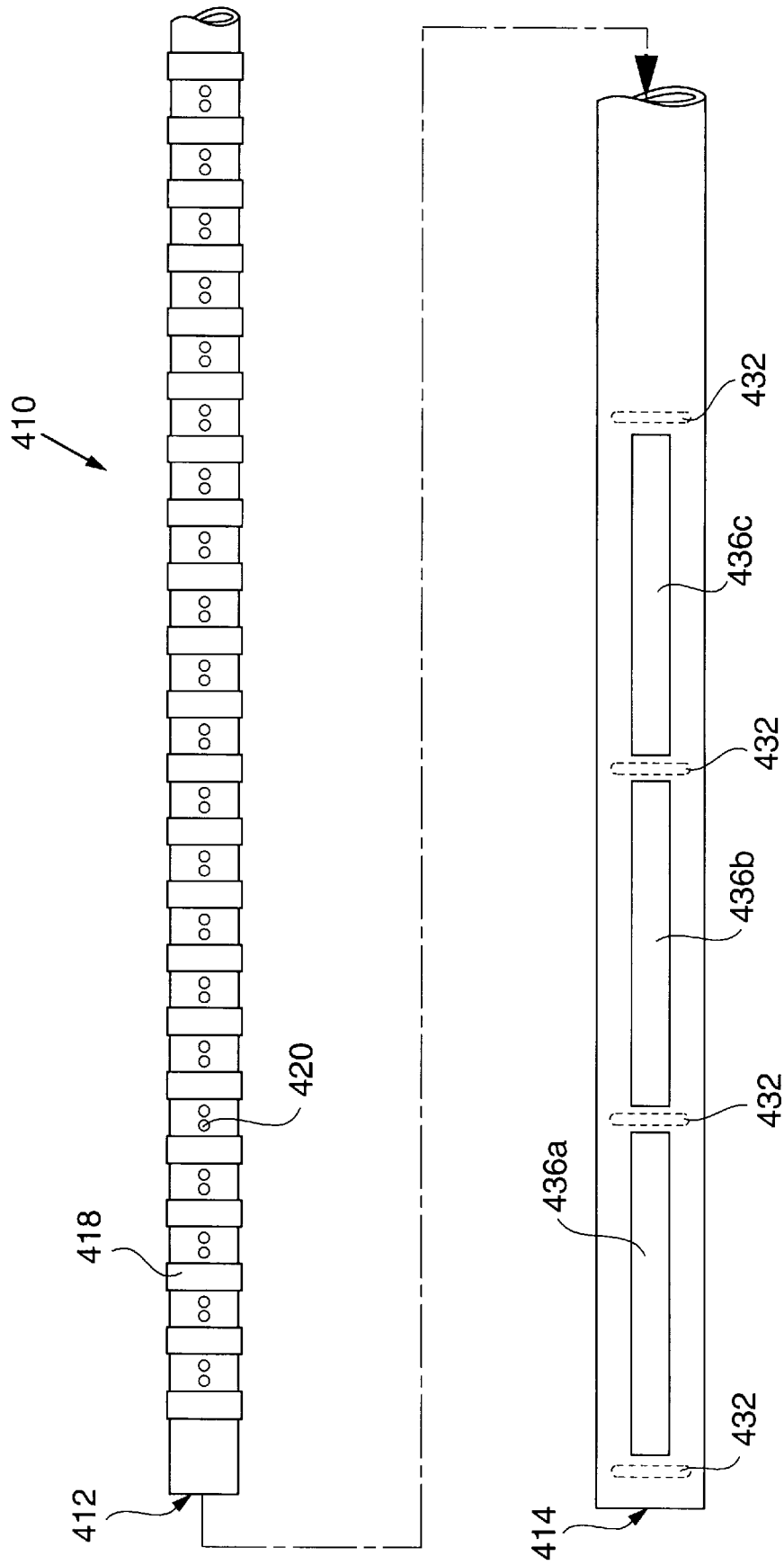
FIG. 20 is a side elevation view of a fifth embodiment of a linear lesion catheter according to the present invention, in which the inner and outer shaft members are separated from one another.
Figure 21:
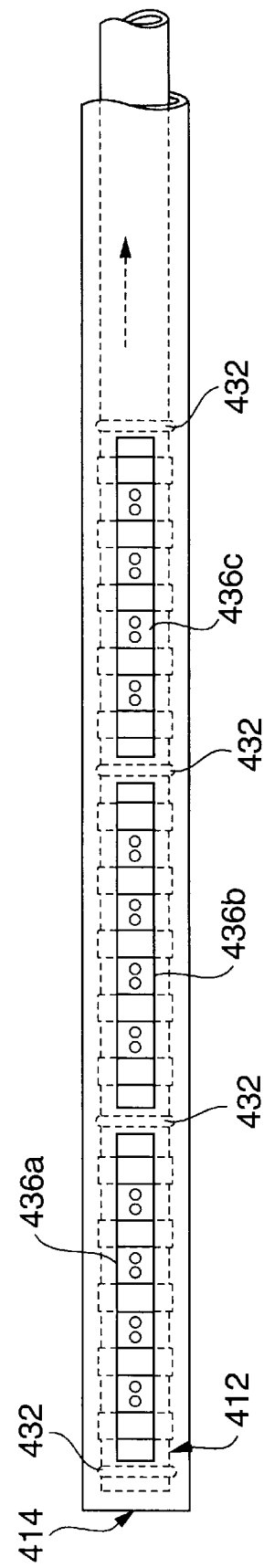
FIG. 21 is a side elevation view of the distal portion of the linear lesion catheter of FIG. 20.

A fifth embodiment of a linear lesion catheter 410 according to the present invention is shown in FIGS. 20–21. The catheter of the fifth embodiment differs from that of the fourth embodiment 310 (FIG. 18) in that three windows 436a, 436b, 436c are provided in place of long window 336 of FIG. 18. Additionally, the electrode array 419 of the fifth embodiment is substantially longer than that of the fourth embodiment. It preferably includes three longitudinally spaced array sections 419a, 419b and 419c, each of which is electrically coupled to a separate lead wire, so that each array section may be separately activated.

Referring to FIG. 21, the entire electrode array 419 preferably extends from the distal end of the window 436a to the proximal end of the window 436c so that the inner and outer shafts 412, 414 can be arranged with each array section 419a, 419b, 419c aligned with its corresponding window 436a, 436b, 436c. Preferably four O-ring seals 432 are positioned within the outer shaft as shown. The seals 432 effectively divide the catheter 410 into three ablation zones, with each zone corresponding to a window/array section pair.

The advantages of this window arrangement are similar to that of the catheter of the fourth embodiment 310. Once the catheter 410 is positioned against the endocardium, the user can choose which ablation zone(s) will be used for ablation by selectively applying RF energy to a select electrode array section 419a, 419b, 419c or to a select group of the array sections. Ablation may be carried out at different ablation zones simultaneously or sequentially without requiring the user to reposition the inner or outer shaft member. A short lesion may be formed by energizing only a single one of the electrode array sections.

Figure 23A:
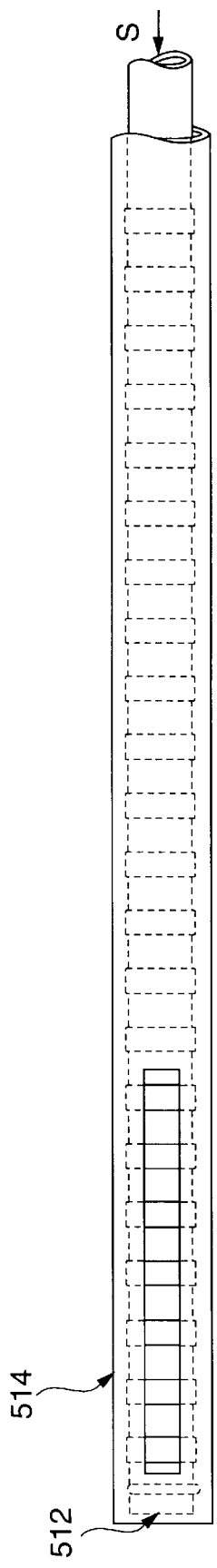
FIGS. 23A through 23C are side elevation views of the distal portion of the linear lesion catheter of FIG. 22A, in which three relative positions of the inner and outer shaft members are shown.
Figure 23B:
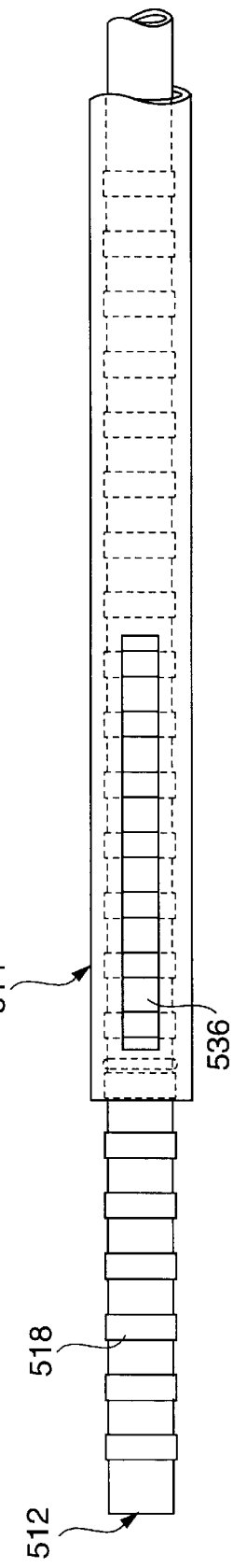
Figure 23C:
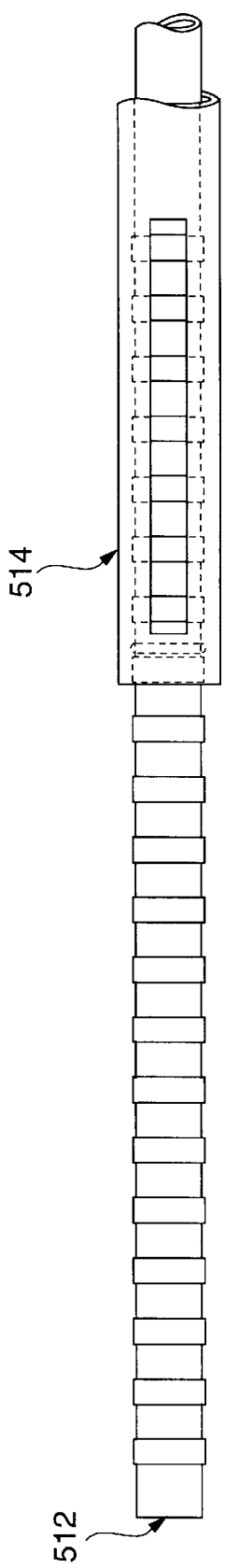

FIGS. 22A–23C show a sixth embodiment of a linear lesion catheter 510 according to the present invention. Catheter 510 of the sixth embodiment is similar to catheter 110 of the second embodiment, but differs primarily in that the electrode array 519 is significantly longer that the window 536. The user therefore may slidably adjust the relative positions of the inner and outer shafts 512, 514 to position the window 536 at a desired region of the electrode array, as shown in FIGS. 23A through 23C.

In the sixth embodiment, the outer shaft 514 is a single lumen device. Fluid such as saline S is introduced into the device via a port at the distal section of the outer shaft 514 and flows through the single lumen 535 of the outer shaft (and thus between the inner and outer shafts).

An o-ring seal 532 (FIG. 22A) is located inside the outer shaft 514 at the distal end of the window 536 to direct the flow of conductive fluid through the window. The embodiment has similar advantages to those of the fourth and fifth embodiments.

Several embodiments of a linear lesion catheter have been described herein. It should be appreciated that these embodiments have been given by way as example and are not intended to limit the scope of the appended claims.

We claim:

1. An apparatus for creating linear lesions in body tissue, the apparatus comprising:

a tubular outer member proportioned for insertion and manipulation through human vessels, the outer member having a distal section and a window formed at the distal section, the window positionable adjacent body tissue and including an area of fluid permeable material;

an elongate inner member telescopically received within the outer member;

at least one electrode carried on the inner member, the inner and outer members slidable between a first relative position in which the window is at least partially in register with the electrode and a second relative position in which the window is not in register with the electrode; and means for delivering ablation energy to the electrode such that, when the inner and outer members are in the first relative position and the window is positioned adjacent body tissue, ablation energy is deliverable to the body tissue through the window.

2. The apparatus of claim 1 wherein the delivering means is for delivering current to the at least one electrode and wherein at least one of the inner and outer members includes a fluid lumen having an exit opening oriented for delivering conductive fluid into contact with the electrode to cause said fluid to create a conductive path between the electrode and the tissue when the electrode is positioned adjacent body tissue.

3. The apparatus of claim 2 wherein the fluid lumen extends through the inner member.

4. The apparatus of claim 2 wherein the fluid lumen extends through the outer member.

5. The apparatus of claim 1 wherein the fluid permeable material is deformable in response to fluid pressure.

6. The apparatus of claim 2 where the window includes an area of the outer member in which at least one opening extends from the fluid lumen to an exterior surface of the distal section.

7. The apparatus of claim 2 further comprising a seal contacting an outer surface of the inner member and an inner surface of the outer member.

8. An apparatus for creating linear lesions in body tissue, the apparatus comprising:
- a tubular outer member proportioned for insertion and manipulation through human vessels, the outer member having a distal section and a window formed at the distal section, the window positionable adjacent body tissue;
- an elongate inner member telescopically received within the outer member;
- a plurality of electrodes arranged on the inner member in an electrode array which has first and second ends and a length, the inner and outer members slidable between a first relative position in which the window is at least partially in register with at least one of the electrodes and a second relative position in which the window is not in register with the at least one of the electrodes, wherein the window has a length which is substantially longer than the length of the electrode array;
- a first seal on the outer surface of the inner member, adjacent to the first end of the array; and
- means for delivering ablation energy to the electrode such that, when the inner and outer members are in the first relative position and the window is positioned adjacent body tissue, ablation energy is deliverable to the body tissue through the window.

9. The apparatus of claim 8, further comprising a second seal attached to the outer surface of the inner member adjacent to the second end of the array.

10. An apparatus for creating linear lesions in body tissue, the apparatus comprising:
- a tubular outer member proportioned for insertion and manipulation through human vessels, the outer member having a distal section and a window formed at the distal section, the window positionable adjacent body tissue;
- an elongate inner member telescopically received within the outer member;
- a plurality of electrodes arranged on the inner member in an electrode array which has a length, the inner and outer members slidable between a first relative position in which the window is at least partially in register with at least one of the electrodes and a second relative position in which the window is not in register with the at least one of the electrodes, wherein the window has first and second ends and a length which is substantially shorter than the length of the electrode array;
- a first seal on the inner surface of the outer member, adjacent to the first end of the window; and
- means for delivering ablation energy to the electrode such that, when the inner and outer members are in the first relative position and the window is positioned adjacent body tissue, ablation energy is deliverable to the body tissue through the window.

11. The apparatus of claim 10, further comprising a second seal attached to the inner surface of the outer member adjacent to the second end of the window.

12. The apparatus of claim 2, wherein:
- the outer shaft includes a plurality of longitudinally spaced windows; and
- the apparatus includes a first seal attached to the inner surface of the outer member.

13. The apparatus of claim 12 wherein:
- the apparatus includes a plurality of electrodes arranged on the inner shaft in an electrode array having first and second ends;
- each window has a pair of ends;
- the seal is adjacent to a distal end of a distalmost one of the windows; and
- the apparatus includes additional seals on the inner surface of the outer member, the additional seals positioned adjacent to the ends of the windows.

14. The apparatus of claim 1, wherein:
- the inner shaft includes a core wire lumen and proximal and distal sections, the distal section having greater flexibility than the proximal section; and
- the apparatus further comprises a core wire having a distal portion with a predetermined non-linear shape, the core wire slidably receivable within the core wire lumen such that when the core wire is introduced into the proximal section of the inner shaft, its distal portion is substantially straightened by the proximal section of the inner shaft, and when said core wire is advanced so that at least a portion of the distal portion is within the distal section of the inner shaft, the catheter is deformed to approximate the non-linear shape of the portion of the distal portion of the core wire that is within the distal section.

15. The apparatus of claim 14, wherein the apparatus further comprises a second core wire having a distal portion with a second predetermined non-linear shape, the second predetermined shape being different from the predetermined shape of the first core wire, and wherein the second core wire is slidably receivable within the lumen.

16. The apparatus of claim 1, further comprising:
- a radiopaque marker positioned adjacent the window.

17. The apparatus of claim 1, wherein the window has first and second ends and wherein the apparatus further includes radiopaque markers adjacent to the first and second ends.

18. The apparatus of claim 17 wherein the radiopaque markers are mapping/pacing electrodes.

19. The apparatus of claim 1, further including a pair of mapping/pacing electrodes positioned adjacent to the window.

20. An apparatus for creating lesions in body tissue, the apparatus comprising:
- a tubular outer member having a distal section and a window formed at the distal section, the window positionable adjacent body tissue;
- an inner member telescopically received within the outer member;
- at least one electrode on the inner member, the inner and outer members slidable between a first relative position in which the window is at least partially in register with the electrode and a second relative position in which the window is not in register with the electrode;
- a source of ablation energy electrically coupled to the electrode such that, when the inner and outer members are in the first relative position and the window is positioned adjacent body tissue, ablation energy is deliverable to the body tissue through the window;
- a fluid lumen in at least one of the inner and outer members, the fluid lumen having an exit opening oriented for delivering conductive fluid into contact with the electrode to cause said fluid to create a conductive path between the electrode and the tissue when the electrode is positioned adjacent body tissue; and a seal contacting an outer surface of the inner member and an inner surface of the outer member.

21. The apparatus of claim 20, wherein:

the apparatus includes a plurality of electrodes arranged on the inner shaft in an electrode array which has first and second ends and a length;

the window has a length which is substantially longer than the length of the electrode array; and the seal is on the outer surface of the inner member, adjacent to the first end of the array.

22. The apparatus of claim 21, further comprising a second seal attached to the outer surface of the inner member adjacent to the second end of the array.

23. The apparatus of claim 20, wherein:

the apparatus includes a plurality of electrodes arranged on the inner shaft in an electrode array which has a length;

the window has first and second ends and a length which is substantially shorter than the length of the electrode array; and the seal is attached to the inner surface of the outer member, adjacent to the first end of the window.

24. The apparatus of claim 23, further comprising a second seal attached to the inner surface of the outer member adjacent to the second end of the window.

25. The apparatus of claim 20, wherein:

the outer shaft includes a plurality of longitudinally spaced windows; and the seal is attached to the outer surface of the inner member, adjacent to the electrode.

26. The apparatus of claim 25 wherein:

the apparatus includes a plurality of electrodes arranged on the inner shaft in an electrode array having first and second ends;

the seal is adjacent to the first end of the array;

the apparatus includes a second seal attached to the outer surface of the inner member, adjacent to the second end of the array.

27. The apparatus of claim 20, wherein:

the inner shaft includes a core wire lumen and proximal and distal sections, the distal section having greater flexibility than the proximal section; and the apparatus further comprises a core wire having a distal portion with a predetermined non-linear shape, the core wire slidably receivable within the core wire lumen such that when the core wire is introduced into the proximal section of the inner shaft, its distal portion is substantially straightened by the proximal section of the inner shaft, and when said core wire is advanced so that at least a portion of the distal portion is within the distal section of the inner shaft, the catheter is deformed to approximate the non-linear shape of the portion of the distal portion of the core wire that is within the distal section.

28. The apparatus of claim 27, wherein the apparatus further comprises a second core wire having a distal portion with a second predetermined non-linear shape, the second predetermined shape being different from the predetermined shape of the first core wire, and wherein the second core wire is slidably receivable within the lumen.

29. A catheter system for ablating body tissue in the form of a linear lesion comprising:

a source of ablation energy;

an inner catheter having an array of ablation electrodes arranged in a linear array adjacent the distal end thereof, said inner catheter further including a conductive wire for coupling the electrodes to the source of ablation energy;

an outer catheter having a central lumen for telescopingly receiving the inner catheter therein, said outer catheter including a longitudinal window formed at the distal end thereof for exposing the electrodes of the inner catheter to the body tissue, the window including an area of fluid permeable material; and a lumen for delivering a conductive fluid from the proximal end of one of the catheters to the distal end thereof and through said window, with said conductive fluid functioning to couple the ablation energy from the electrodes to the body tissue.

30. The catheter system of claim 29 wherein the lumen extends through the inner catheter.

31. The catheter system of claim 29 wherein the lumen extends through the outer catheter.

32. The catheter system of claim 29, wherein:

the inner catheter includes a core wire lumen and proximal and distal sections, the distal section having greater flexibility than the proximal section; and the apparatus further comprises a core wire having a distal portion with a predetermined non-linear shape, the core wire slidably receivable within the core wire lumen such that when the core wire is introduced into the proximal section of the inner catheter, its distal portion is substantially straightened by the proximal section of the inner catheter, and when said core wire is advanced so that at least a portion of the distal portion is within the distal section of the inner shaft, the catheter is deformed to approximate the non-linear shape of the portion of the distal portion of the core wire that is within the distal section.

33. The catheter system of claim 29 wherein the ablation electrodes include ring electrodes longitudinally spaced on the inner catheter.

* * * * *